United States Patent
Krekeler et al.

(10) Patent No.: US 10,485,799 B2
(45) Date of Patent: Nov. 26, 2019

(54) PHARMACEUTICAL COMPOSITION OF VORTIOXETINE HYDROBROMIDE COMPRISING VORTIOXETINE HYDROBROMIDE IN A POLYETHYLENE OXIDE MATRIX

(71) Applicant: Hexal AG, Holzkirchen (DE)

(72) Inventors: Andreas Krekeler, Holzkirchen (DE); Dimitri Neumann, Holzkirchen (DE); Michael Sedlmayr, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 15/386,566

(22) Filed: Dec. 21, 2016

(65) Prior Publication Data

US 2017/0182034 A1 Jun. 29, 2017

(30) Foreign Application Priority Data

Dec. 23, 2015 (EP) .................................. 15202425

(51) Int. Cl.
*A61K 31/495* (2006.01)
*A61K 47/34* (2017.01)
*A61K 47/38* (2006.01)
*A61K 9/20* (2006.01)

(52) U.S. Cl.
CPC .......... *A61K 31/495* (2013.01); *A61K 9/2031* (2013.01); *A61K 9/2054* (2013.01); *A61K 47/34* (2013.01); *A61K 47/38* (2013.01)

(58) Field of Classification Search
CPC ...... A61K 31/445; A61K 47/34; A61K 47/38; A61K 31/495
USPC ...................................................... 514/255.03
See application file for complete search history.

(56) References Cited

FOREIGN PATENT DOCUMENTS

| WO | 2004084869 | A1 | 10/2004 | |
|---|---|---|---|---|
| WO | 2007144005 | A1 | 12/2007 | |
| WO | 2011023194 | A2 | 3/2011 | |
| WO | WO 2011023194 | A2 * | 3/2011 | ........... A61K 9/2054 |
| WO | 2014044721 | A1 | 3/2014 | |
| WO | 2014177491 | A1 | 11/2014 | |

OTHER PUBLICATIONS

Extended European Search Report for European Patent App. No. 15202425.3, dated Mar. 4, 2016, 5 pages.

* cited by examiner

*Primary Examiner* — Craig D Ricci
*Assistant Examiner* — Janet L. Coppins
(74) *Attorney, Agent, or Firm* — Luedeka Neely Group, P.C.

(57) ABSTRACT

The present invention relates to a solid oral pharmaceutical composition comprising vortioxetine hydrobromide in a matrix formed from at least one polyethylene oxide and optionally one or more further matrix forming polymers.

9 Claims, 1 Drawing Sheet

PHARMACEUTICAL COMPOSITION OF VORTIOXETINE HYDROBROMIDE COMPRISING VORTIOXETINE HYDROBROMIDE IN A POLYETHYLENE OXIDE MATRIX

This application claims the benefit of the earlier filing date of European patent application 15202425.3, filed Dec. 23, 2015.

FIELD OF THE INVENTION

The present invention relates to a pharmaceutical composition comprising vortioxetine hydrobromide in a polyethylene oxide matrix, a process for the preparation thereof, and use thereof.

BACKGROUND OF THE INVENTION

Vortioxetine (also known under the name Lu-AA21004 and the tradename Brintellix®) has the chemical name 1-{2-[(2,4-dimethylphenyl)sulfanyl]phenyl}piperazine, the structure of which is

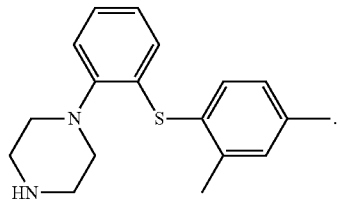 [SMILES: Cc1ccc(Sc2ccccc2N2CCNCC2)c(C)c1]

Recently, the FDA approved vortioxetine for the treatment of adults with major depressive disorder. The finished product is presented as immediate-release film-coated tablet containing 5 to 20 mg of Vortioxetine (as crystalline hydrobromide salt) as the active substance. Vortioxetine exhibits polymorphism and appears in several polymorphs. A method of producing crystalline vortioxetine and several acid addition salts thereof is disclosed in WO 2007/144005 A1.

Nausea is reported to be the most common adverse reaction and its frequency was dose-related (cf. Prescribing Information Brintellix®). According to WO 2011/023194, the amount of adverse events can be lowered, if vortioxetine is not released in the stomach but in the intestine (enteric coated tablets or enteric coated multiparticulate compositions are suggested).

However, the inventors found that these enterically coated, gastro-resistant formulations show highly variable in-vitro release profiles of vortioxetine hydrobromide (i.e. are highly variable in vivo performance), depending on the individual pH in the intestine of the patient. This problem was further investigated by the present inventors, who also realized that there is the risk of dose dumping if vortioxetine hydrobromide is provided in such a prior art formulation.

It has been unexpectedly found by the present inventors that the above disadvantages can be overcome by providing vortioxetine hydrobromide in a matrix formed from at least one polyethylene oxide and optionally one or more further matrix forming polymers.

Based on these findings, the inventors developed pharmaceutical compositions with an advantageous dissolution profile of vortioxetine hydrobromide that enables controlled release of vortioxetine hydrobromide independent of the pH value of the environment, thereby allowing an excellent balance between reduced adverse events and release profile of the vortioxetine hydrobromide upon administration to a patient.

The present invention therefore provides a solid oral pharmaceutical composition comprising vortioxetine hydrobromide in a matrix formed from at least one polyethylene oxide and optionally one or more further matrix forming polymers.

The present invention also provides a process for the preparation of the solid oral pharmaceutical composition comprising vortioxetine hydrobromide in a matrix formed from at least one polyethylene oxide and optionally one or more further matrix forming polymers. The process comprises the steps of forming a blend of vortioxetine hydrobromide and at least one polyethylene oxide and optionally further matrix forming polymers and/or pharmaceutical acceptable excipients, and compressing the blend.

The present invention also provides a solid oral pharmaceutical composition comprising vortioxetine hydrobromide in a matrix formed from at least one polyethylene oxide and optionally one or more further matrix forming polymers for use in the treatment of a disease selected from affective disorders, depression, major depressive disorder, postnatal depression, depression associated with bipolar disorder, Alzheimer's disease, psychosis, cancer, age or Parkinson's disease, anxiety, general anxiety disorder, social anxiety disorder, obsessive compulsive disorder, panic disorder, panic attacks, phobia, social phobia, agoraphobia, stress urinary incontinence, emesis, irritable bowel syndrome, eating disorders, chronic pain, partial responders, treatment resistant depression, Alzheimer's disease, cognitive impairment, attention deficit hyperactivity disorder, melancholia, posttraumatic stress disorder, hot flushes, sleep apnea, alcohol, nicotine or carbohydrate craving, substance abuse and alcohol and drug abuse.

DETAILED DESCRIPTION OF THE INVENTION

Figure 1:
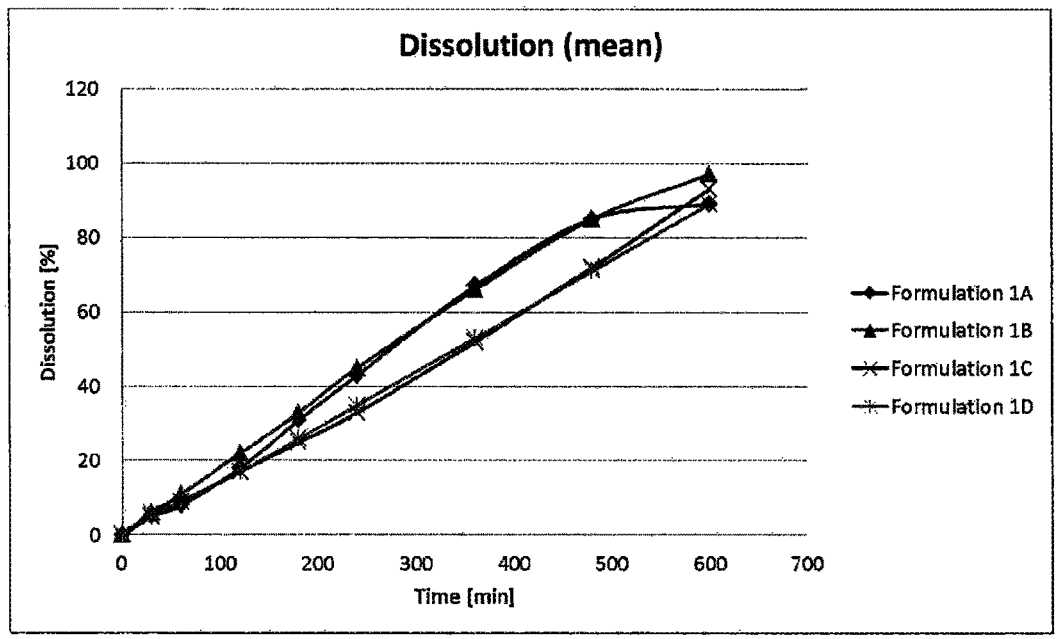
FIG. 1: Dissolution profile of Formulations 1A, 1B, 1C and 1D according to Example 1.

The term "pharmaceutical composition", as used herein, refers to a composition comprising at least one pharmaceutically active ingredient and one or more pharmaceutically acceptable excipients. Herein, the pharmaceutically active ingredient which is vortioxetine hydrobromide provides the therapeutic effect for the treatment of a disease in a patient.

The term "Vortioxetine hydrobromide" means the pharmaceutically acceptable acid addition salt of vortioxetine with hydrochlorid acid. Pharmaceutically acceptable salts are intended to indicate acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic acids, such as hydrochloric, hydrobromic, sulfuric, sulfamic, phosphoric and nitric acids. Although distinct mention is made of the hydrobromide acid salt, the composition of the present invention can comprise any pharmaceutically acceptable salt of vortioxetine instead of salts made from hydrobromic acid. Particular mention is made of salts made from lactic acid. Particular mention is also made of salts made from acetic acid.

Pharmaceutically acceptable excipients are e.g. matrix forming polymers.

The term "molecular weight" or "Mw" as used herein refers to the weight average molecular weight of the corresponding polymer, as determined by GPC if nothing else is explicitly stated or obvious under the circumstances. How to determine the Mw of polyethylene oxide by GPC, the conditions, solvents etc. to be used, are well known to the skilled person. The absolute value for Mw can also be determined by viscosimetry as is also known in the art.

The term "about" or "approximate" used in particular in conjunction with the molecular weight (Mw) of a polymer such as polyethylene oxide, addresses the fact that the molecular weight of a polymer cannot exactly be determined and underlies measurement fluctuations. For the purpose of the present invention, the term "about" or "approximate" used in conjunction with the molecular weight (Mw) of a polymer such as polyethylene oxide thus refers to the molecular weight (Mw) of the polymer ±20%, preferably ±10%.

Unless otherwise noted or obvious in the circumstances, percentage terms used herein refer to weight/weight (w/w) percentages.

The term "release", as used herein, refers to the release of the pharmaceutically active ingredient, i.e. vortioxetine hydrobromide, from a dosage form comprising the pharmaceutical composition after exposing same to conditions whereupon the pharmaceutically active ingredient is released from the dosage form. The term "release rate" or "release profile" refers to the (percentage) amount released per time unit from the dosage form comprising the pharmaceutical composition. For the purpose of the invention of this invention, the in-vivo release profile will be assumed as corresponding to the in-vitro dissolution profile as explained below and will be measured as explained below and in the examples by means of the (in-vitro) dissolution rate. Determining the dissolution profile of the pharmaceutical composition of the present invention can be done e.g. by using the USP Dissolution Apparatus 2 (Paddle). With respect to details of the process it is referred to the dissolution tests described in the US Pharmacopeial Convention <711> and/or the European Pharmacopeia (2.9.3.).

The term "controlled release" as used herein indicates that the pharmaceutically active ingredient of the dosage form is released from the dosage form comprising the pharmaceutical composition over a prolonged (extended) period of time upon administration of the dosage form compared to an immediate release formulation of the pharmaceutically active ingredient.

Determining the dissolution profile of the pharmaceutical composition of the present invention can be done as follows: The pharmaceutical composition is placed in 900 mL of 0.1 N hydrochloric acid, stirred at 50 rpm at a temperature of 37±0.5° C. The dissolution profile is then determined e.g. by taking aliquots at defined time points (e.g. 30, min, 60 min, 120 min, 180 min, 240 min, 360 min, 480 min, and 600 min), followed by measuring the vortioxetine hydrobromide amount contained in the aliquots in a suitable assay. The dissolution of vortioxetine hydrobromide from the composition of the present invention is essentially independent from the pH, i.e. 0.05 M $KH_2PO_4$ buffer at a temperature of 37±0.5°° C. and a pH of 6.8±0.05 can alternatively be used for determining the dissolution profile of the composition of the invention.

The dissolution profile or release profile of vortioxetine hydrobromide from the pharmaceutical composition of the present invention is preferably as follows (measured as described above in 0.1 N hydrochloric acid, stirred at 50 rpm at a temperature of 37±0.5° C.):
1-20% (w/w), preferably 3-15% (w/w) after 30 minutes,
3-40% (w/w), preferably 6-25% (w/w) after 120 minutes,
at least 75% (w/w), preferably at least 85% after 600 minutes, each based on the total amount of vortioxetine hydrobromide in the pharmaceutical composition of the invention (at the beginning of the measurement (t=0).

The vortioxetine hydrobromide that is used in the pharmaceutical composition of the present invention is preferably crystalline.

WO 2007/144005 discloses several crystalline forms including alpha, beta and gamma, and WO 2014/044721 discloses a further crystalline form of vortioxetine hydrobromide having an XRPD pattern with characteristic peaks (expressed in 2θ±0.2° 2θ (CuKα radiation)) at 5.5°, 14.8°, 16.7° and 20.0°. Generally any crystalline form of vortioxetine hydrobromide, such as the ones described herein above can be used to prepare the pharmaceutical composition of the invention. Advantageously, the release of vortioxetine hydrobromide from the pharmaceutical composition of the present invention is independent of the crystalline form of vortioxetine hydrobromide in the composition. In the composition of the present invention, vortioxetine hydrobromide can advantageously be used in any of its crystalline forms without adversely influencing the dissolution profile.

The pharmaceutical composition of the present invention comprises a matrix wherein the vortioxetine hydrobromide is embedded. The amount of the vortioxetine hydrobromide in the matrix is preferably 2-25% (w/w), more preferably 2-20% (w/w), even more preferably 5-15% (w/w), and particularly preferably 5-10% (w/w), each based on the total weight of the matrix.

The matrix is formed from at least one polyethylene oxide as the matrix forming polymer, and optionally one or more further matrix forming polymers. The matrix can thus be formed from one or more polyethylene oxides and further matrix forming polymers. However, it is preferred that the matrix only comprises one or more polyethylene oxides as the matrix forming polymer. More preferably, the matrix is formed from one polyethylene oxide of a particular molecular weight (Mw) as the matrix forming polymer.

Polyethylene oxides, as used in the pharmaceutical composition of the present invention, are nonionic, hydrophilic polymers, which hydrate and swell rapidly upon exposure to water or gastric juices to form hydrogels with properties ideally suited for an advantageous dissolution profile of vortioxetine hydrobromide. They also have the advantage that they are available in various molecular weight (Mw) grades so that the release of vortioxetine hydrobromide from the pharmaceutical of the present invention can be adjusted by selecting a polyethylene oxide of a particular molecular weight (Mw) in a particular amount. Polyethylene oxides furthermore do not interact with the pharmaceutically active ingredient vortioxetine hydrobromide so that the release of vortioxetine hydrobromide can be adjusted in a reproducible manner. Finally, polyethylene oxides are cheap and readily available. Examples for commercial polyethylene oxides which can be used in accordance with the present invention include POLYOX Water-soluble Resins marketed by The Dow Chemical Company, e.g. POLYOX WSR N-10 (Mw about 100,000), POLYOX WSR N-80 (Mw about 200.000), POLYOX WSR N-750 (Mw about 300,000), POLYOX WSR-205 (Mw about 600,000), POLYOX WSR-1105 (Mw about 900.000), and POLYOX VVSR N-12K (Mw about 1,000,000).

The amount of the polyethylene oxide in the pharmaceutical composition according to the present invention can influence the dissolution profile of vortioxetine hydrobromide.

In one embodiment, in the matrix of the pharmaceutical composition of the present invention, the matrix forming polymers (i.e. polyethylene oxides and further optional matrix forming polymers) are preferably present in an amount of 75-98% (w/w) based on the total weight of the matrix. More preferably, the matrix forming polymers are present in an amount of 85-95% (w/w), based on the total weight of the matrix.

In one embodiment, in the matrix of the pharmaceutical composition of the present invention, the at least one polyethylene oxide is preferably present in an amount of 75-98% (w/w) based on the total weight of the matrix. More preferably, the at least one polyethylene oxide is present in an amount 85-95% (w/w), based on the total weight of the matrix.

In another embodiment, in the matrix of the pharmaceutical composition of the present invention, the at least one polyethylene oxide is preferably present in an amount of 10-98% (w/w) based on the total weight of the matrix. More preferably, the at least one polyethylene oxide is present in an amount of 20-97% (w/w), 30-96% (w/w), and 40-95% (w/w), each based on the total weight of the matrix. It is particularly preferable that the at least one polyethylene oxide is present in an amount of 45-95% (w/w) based on the total weight of the matrix.

In a preferred embodiment of the pharmaceutical composition of the present invention, the ratio of the vortioxetine hydrobromide to the at least one polyethylene oxide in the matrix is 1:3-50 , preferably 1:5-20.

As mentioned above, also the molecular weight (Mw) of the at least one polyethylene oxide forming the matrix can influence the dissolution profile of vortioxetine hydrobromide in the pharmaceutical composition of the present invention. Thus, for obtaining an advantageous dissolution profile of vortioxetine hydrobromide, a polyethylene oxide with a suitable weight average molecular weight should be used.

In a preferred embodiment of the present invention, the polyethylene oxide has a molecular weight (Mw) of at least about 100,000, more preferably about 200,000, even more preferably about 300,000, and particularly preferably at least about 400,000. On the other hand, the molecular weight (Mw) of the at least one polyethylene oxide used in the pharmaceutical composition of the present invention should not exceed about 1,000,000, and preferably not exceed about 900,000. In particular the use of polyethylene oxides with a molecular weight (Mw) of 300,000 to 1,000,000, preferably 400,000 to 1,000,000 allows a dissolution rate of vortioxetine hydrobromide from the composition of the present invention as defined herein.

Further matrix forming materials can optionally be present in the matrix. Further pharmaceutically acceptable matrix forming materials are known in the art, e.g. hydrophilic polymers including Hydroxypropylmethylcellulose (HPMC), Hydroxypropylcellulose (HPC), Hydroxyethyl cellulose (HEC), Xanthan gum, Sodium alginate, and cross-linked homopolymers and copolymers of Acrylic acid. In one embodiment, the matrix of the pharmaceutical composition further contains one or more matrix forming materials selected from the group consisting of Polyhydroxyethylemethylacrylate (PHEMA), Cross-linked polyvinyl alcohol (PVA), Cross-linked polyvinyl pyrrolidone (PVP), Polyacrylamide (PA), Polyethyleneglycol (PEG), polyvinyl alcohol (PVA), Polyvinylpyrrolidone (PVP), Hydroxypropyl methyl cellulose (HPMC), Polylactic acid (PLA), Polyglycolic acid (PGA), Polycaprolactone (PCL), Polyanhydrides, Polyorthoesters, Polyethylene vinyl acetate (PVA), Polydimethylsiloxane (PDS), Polyether urethane (PEU), Polyvinyl chloride (PVC), Cellulose acetate (CA), Ethyl cellulose (EC), Polycarbophil, Sodium carboxymethyl cellulose, Polyacrylic acid, Tragacanth, Methyl cellulose, Pectin, Xanthan gum, Guar gum, Karaya gum, and Locust bean gum. Preferably, the matrix consists of polyethylene oxide and optionally one or more pharmaceutically acceptable excipients.

It is preferred that the matrix of the pharmaceutical composition of the present invention is formed from one or more polyethylene oxides as the matrix forming polymers only, i.e. exclusively contains vortioxetine hydrobromide and one or more polyethylene oxides as the matrix forming polymers, i.e. does not contain further matrix forming polymers besides the at least one polyethylene oxide. However, in a further preferred embodiment of the pharmaceutical composition of the present invention, the matrix of the present invention contains vortioxetine hydrobromide, the at least polyethylene oxide and one or more pharmaceutically acceptable excipients.

Pharmaceutically acceptable excipients that can be used in the pharmaceutical composition of the present invention are pharmaceutically acceptable excipients known in the field, which include, but are not limited to antioxidants, dry binders, fillers, glidants, lubricants and surfactants. In general, the one or more pharmaceutically acceptable excipients are preferably contained in an amount of about 0.01-70% (w/w), more preferably of about 0.1-65% (w/w), even more preferably 0.5-60%, and particularly preferably 1-55% (w/w), based on the total weight of the matrix. In another embodiment, the one or more pharmaceutically acceptable excipients are preferably contained in an amount of about 0-25% (w/w), more preferably of about 0-10% (w/w), based on the total weight of the matrix.

Examples of antioxidants include water soluble antioxidants such as ascorbic acid, sodium sulfite, metabisulfite, sodium miosulfite, sodium formaldehyde, sulfoxylate, isoascorbic acid, isoascorbic acid, cysteine hydrochloride, 1,4-diazobicyclo-(2,2,2)-octane, and mixtures thereof.

Examples of pharmaceutically fillers and dry binders include, but are not limited to celluloses and derivatives thereof, confectioner's sugar, compressible sugar, dextrates, dextrin, dextrose, inorganic fillers (such as calcium phosphate, calcium hydrogen phosphate), lactose, mannitol, microcrystalline cellulose, polysaccharides, powdered cellulose, sorbitol, starches, sucrose and talc. Examples of celluloses and derivatives thereof include for example, microcrystalline cellulose, e.g., AVICEL PH from FMC (Philadelphia, Pa.). Particularly preferred is microcrystalline cellulose, e.g., AVICEL PH 101 from FMC (Philadelphia, Pa.).

Examples of glidants and lubricants include, but are not limited to, colloidal silica, magnesium trisilicate, talc, magnesium stearate, aluminum stearate, calcium stearate, magnesium oxide and polyethylene glycol. Especially preferred is magnesium stearate, which is preferably present in an amount of 0.01-10% (w/w), more preferably in an amount of 0.1-7%, and particularly preferably in an amount of 0.5-2% (w/w), based on the total weight of the matrix.

Surfactants include, but are not limited to, fatty acid and alkyl sulfonates; benzethonium chloride, e.g., HYAMINE 1622 from Lonza, Inc. (Fairlawn, N.J.); polyoxyethylene sorbitan fatty acid esters, e.g., the TWEEN Series from Unigema (Wilmington, Del.); and natural surfactants, such as sodium taurocholic acid, 1-palmitoyl-2-Sn-glycero-3-phosphocholine, lecithin and other phospholipids.

Further pharmaceutical acceptable excipients that can be present in the pharmaceutical composition of the present invention are organic acids which include but are not limited to tartaric acid, fumaric acid, succinic acid, citric acid, malic acid, glutamic acid, aspartic acid or one of the hydrates thereof. Organic acids as excipients can influence the dissolution profile of vortioxetine hydrobromide in the pharmaceutical composition of the present invention. Especially preferred is tartaric acid.

In another embodiment, the pharmaceutical composition of the present invention comprises vortioxetine hydrobromide in a matrix formed of at least one polyethylene oxide as described above, wherein the matrix further comprises microcrystalline cellulose as one pharmaceutically acceptable excipient, wherein microcrystalline cellulose is preferably present in an amount of 10-50% (w/w), more preferably in an amount of 15-45% (w/w), and particularly preferably in an amount of 20-40% (w/w), each based on the total weight of the matrix. In another embodiment, the pharmaceutical composition of the present invention comprises vortioxetine hydrobromide in a matrix formed of at least one polyethylene oxide as described above, wherein the matrix further comprises microcrystalline cellulose as one pharmaceutically acceptable excipient, wherein microcrystalline cellulose is preferably present in an amount of 0-30% (w/w), more preferably in an amount of 0-25% (w/w), and particularly preferably in an amount of 0-10% (w/w), each based on the total weight of the matrix. In another embodiment, the pharmaceutical composition of the present invention comprises vortioxetine hydrobromide in a matrix formed of at least one polyethylene oxide as described above, wherein the matrix further comprises microcrystalline cellulose as one pharmaceutically acceptable excipient, wherein microcrystalline cellulose is preferably present in an amount of 5-30 (w/w), more preferably in an amount of 5-25% (w/w), and particularly preferably in an amount of 5-10% (w/w), each based on the total weight of the matrix.

The microcrystalline cellulose can contribute to obtaining a dissolution rate of vortioxetine hydrobromide from the composition of the present invention as defined herein. This in particular can apply if polyethylene oxides with a relatively low molecular weight (Mw) of e.g. 100,000 and 200,000 are used as the matrix forming materials. However, also for matrices wherein polyethylene oxides with a higher molecular weight (Mw) such as 300,000 or 400,000 to 1,000,000 are used, microcrystalline cellulose as an additional ingredient of the matrix can contribute to obtaining a dissolution profile of vortioxetine hydrobromide from the pharmaceutical composition of the present invention as defined herein.

The pharmaceutical composition of the present invention can consist exclusively of the matrix as defined above. On the other hand, the pharmaceutical composition of the present invention can also comprise one or more pharmaceutically acceptable coatings. Preferably, the pharmaceutical composition of the present invention is provided without coating.

The pharmaceutical composition of the present invention provides an advantageous dissolution profile for vortioxetine hydrobromide as defined above. The dissolution rate of the pharmaceutical composition of the present invention is essentially independent from the pH value of the environment, thereby allowing controlled release of vortioxetine hydrobromide upon administration of the pharmaceutical composition to a human patient in both the stomach and the intestine, which prevents fluctuations in the release of vortioxetine hydrobromide and minimizes the risk of dose dumping.

The advantageous dissolution profile of the pharmaceutical composition of the present invention as described above particularly allows that only minor amounts of vortioxetine hydrobromide are released in the stomach or under conditions similar to those in the stomach passage of a human patient (e.g. 0.1 N hydrochloric acid at a temperature of 37±0.5° C. for 120 min), while the major amount of vortioxetine hydrobromide is released in the intestine of a human patient or under conditions similar to those in the intestine of a human patient (e.g. 0.05 M $KH_2PO_4$ buffer at a temperature of 37±0.5° C. and a pH of 6.8±0.05). The release of vortioxetine hydrobromide in the stomach passage is thus minimized, thereby reducing adverse effects in a patient.

In a preferred embodiment of the present invention, not more than 40% (w/w), more preferably not more than 25% (w/w) of the vortioxetine hydrobromide, based on the total amount of vortioxetine hydrobromide in the pharmaceutical composition, is released in the stomach of a human patient within 2 hours upon administration of the composition, and under conditions similar to those in the stomach passage of a human patient (e.g. 900 mL of 0.1 N hydrochloric acid, stirred at 50 rpm at a temperature of 37±0.5° C. for 2 hours), respectively, whereas the major amount of vortioxetine hydrobromide, i.e. more than 70% (w/w), preferably more than 85% (w/w), based on the total amount of vortioxetine hydrobromide in the pharmaceutical composition is released in the intestine, and under conditions similar to those in the intestine (e.g, 900 mL of 0.05 M $KH_2PO_4$ buffer, stirred at 50 rpm at a temperature of 37±0.5° C. at a pH of 6.8±0.05), respectively.

The process for the preparation of the pharmaceutical composition according to the invention comprises the steps of forming a blend of vortioxetine hydrobromide, at least one polyethylene oxide, and optionally further matrix forming polymers and/or pharmaceutically acceptable excipients as described above, followed by compressing the blend.

In the direct compression method, all materials are weighed and passed through a mesh sieve. Alternatively, the materials are milled or even micronized and will have a particle size distribution suitable for direct compression. Next, the materials are mixed in a mixing device, e.g. a cubic mixer. Then the resultant mixture is directly compressed to tablets in a suitable tablet press.

The process of the present invention allows an easy, straight-forward and economical manufacturing of the pharmaceutical composition of the present invention.

The pharmaceutical composition described above can be used in the treatment of a disease selected from affective disorders, depression, major depressive disorder, postnatal depression, depression associated with bipolar disorder, Alzheimer's disease, psychosis, cancer, age or Parkinson's disease, anxiety, general anxiety disorder, social anxiety disorder, obsessive compulsive disorder, panic disorder, panic attacks, phobia, social phobia, agoraphobia, stress urinary incontinence, emesis, irritable bowel syndrome, eating disorders, chronic pain, partial responders, treatment resistant depression, Alzheimer's disease, cognitive impairment, attention deficit hyperactivity disorder, melancholia, posttraumatic stress disorder, hot flushes, sleep apnea, alcohol, nicotine or carbohydrate craving, substance abuse and alcohol and drug abuse.

For the above-mentioned indications, the appropriate dosage will vary depending on, for example, the host, the mode of administration, the nature and severity of the condition, disease or disorder or the effect desired. Vortioxetine hydrobromide may be conveniently administered in a unit dose form comprising about 1-50 mg of vortioxetine hydrobromide. The total daily dose is expected to be in the range of about 5-20 mg of vortioxetine hydrobromide.

Vortioxetine hydrobromide provided in a pharmaceutical composition according to the invention has an excellent balance between adverse events and release profile. The matrix of the pharmaceutical composition as described above allows a controlled dissolution profile of vortioxetine hydrobromide as defined herein, which is essentially independent of the pH value of the medium. In consequence, only small amounts of vortioxetine hydrobromide are released in the stomach passage of a human patient where vortioxetine hydrobromide can lead to nausea. The major amount of the vortioxetine hydrobromide is released in the intestine.

The pharmaceutical compositions of the present invention are provided as solid oral dosage form. Solid oral dosage forms include, but are not limited to tablets, hard or soft capsules, caplets, lozenges, pills, mini-tablets, pellets, beads or granules (e.g. packaged in sachets).

Tablets, pellets and granules may be either film coated or enteric coated according to methods known in the art. Tablets can be optionally coated with a functional or non-functional coating as known in the art. Examples of coating techniques include, but are not limited to, sugar coating and film coating.

The present invention will be explained in more detail with the following examples, which are not to be interpreted as limiting.

EXAMPLES

Example 1

Preparation of Vortioxetine Hydrobromide Formulations Comprising a Polyethylene Oxide Matrix Four formulations (1A, 1B, 1C, 1D) were produced using polyethylene oxides with different molecular weights (POLYOX WSR N-750, approximate molecular weight (Mw) 300,000; POLYOX WSR 205, approximate molecular weight (Mw) 600,000; POLYOX WSR 1105, approximate molecular weight 900,000; POLYOX WSR N-12K, approximate molecular weight 1,000,000; The Dow Chemical Company) as the matrix forming polymer.

Crystalline vortioxetine hydrobromide in the beta form (a method for the production is described in example 4c of WO 2007/144005) and polyethylene oxide were sieved via 0.8 mm and mixed for 20 min. Magnesium stearate was sieved via 0.5 mm, added to the premixture, which was again mixed for 3 minutes. The final blend was compressed using a 7 mm tooling round to a hardness of 60-85 N. The batch size was 150 tablets.

The composition of Formulations 1A, 1B, 1C and 1D is summarized in the following Table 1:

TABLE 1

| Ingredient | Formulation 1A [mg] | Formulation 1B [mg] | Formulation 1C [mg] | Formulation 1D [mg] |
|---|---|---|---|---|
| Vortioxetine hydrobromide | 6.36 | 6.36 | 6.36 | 6.36 |
| Polyethylene oxide | 142.14 (WSR N-750) | 142.14 (WSR 205) | 142.14 (WSR 1105) | 142.14 (WSR N-12K) |
| Magnesium stearate | 1.50 | 1.50 | 1.50 | 1.50 |
| Σ | 150.0 | 150.0 | 150.0 | 150.0 |

The dissolution profiles of formulations 1A, 1B, 1C and 1D were measured using an USP Paddle Apparatus II in 900 mL of 0.1 N hydrochloric acid, stirred at 50 rpm at a temperature of 37±0.5° C.

The dissolution profiles of formulations 1A, 1B, 1C and 1D are depicted in FIG. 1. The release of vortioxetine hydrobromide during the first 120 min (time of stomach transit) is 17-22% (w/w), based on the total weight amount of vortioxetine hydrobromide in the formulation. A beneficial (linear) dissolution profile as defined herein is observed.

Comparative Example 1

Preparation of Vortioxetine Hydrobromide Formulations Comprising a Methylcellulose Ether-based Matrix Three formulations (2A, 2B, 2C) were produced using different methylcellulose ethers (HPMC) with different viscosities (mPa·s; 2% in water at 20° C.) (Methocel E4M, viscosity of 3,817; Methocel K15M, viscosity of 19,028; and Methocel K100M, viscosity of 107,500; each marketed by Dow Chemical Company) as the matrix forming polymer.

Crystalline vortioxetine hydrobromide in the beta form (a method for the production is described in example 4c of WO 2007/144005), methylcellulose ether and microcrystalline cellulose (Avicel PH101) were sieved via 0.8 mm and mixed for 20 min. 225 mg magnesium stearate was sieved via 0.5 mm, added to the premixture, which was again mixed for 3 minutes. The final blend was compressed using a 8 mm tooling round to a hardness of 40-50 N. The batch size was 150 tablets.

The composition of Formulations 2A, 2B and 2C is summarized in the following Table 2;

TABLE 2

| Ingredient | Formulation 2A [mg] | Formulation 2B [mg] | Formulation 2C [mg] |
|---|---|---|---|
| Vortioxetine hydrobromide | 6.36 | 6.36 | 636 |
| HPMC | 30.00 (Methocel E4M) | 30.00 (Methocel K15M) | 30.00 (Methocel K100M) |
| Avicel PH101 | 112.14 | 112.14 | 112.14 |
| Magnesium stearate | 1.50 | 1.50 | 1.50 |
| Σ | 150.0 | 150.0 | 150.0 |

The dissolution profiles of formulations 2A, 2B, and 2C were measured using an USP Paddle Apparatus II in 900 mL of 0.1 N hydrochloric acid, stirred at 50 rpm at a temperature of 37±0.5° C.

Figure 2:
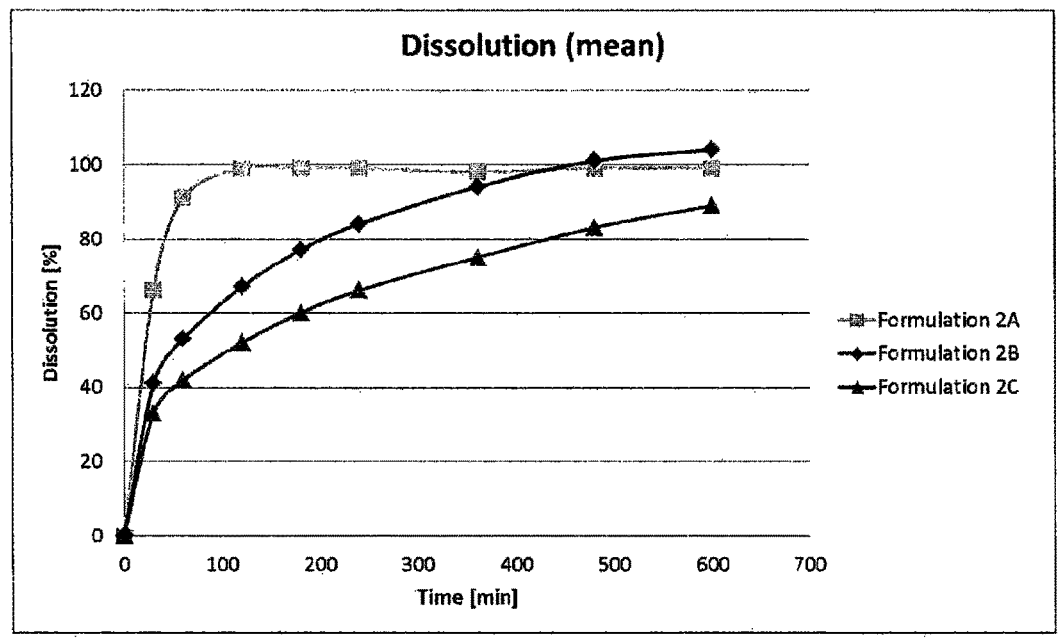
FIG. 2: Dissolution profile of Formulations 2A, 2B, and 2C according to Comparative Example 1.

The dissolution profiles of formulations 2A, 2B, and 2C are depicted in FIG. 2. The release of vortioxetine hydrobromide during the first 120 min (time of stomach transit) is 50-100% (w/w), based on the total weight amount of vortioxetine hydrobromide in the formulation.

It has accordingly been shown in Example 1 that polyethylene oxides of different molecular weights can be used as matrix forming polymers in a pharmaceutical composition comprising vortioxetine hydrobromide, wherein an advantageous dissolution profile of vortioxetine hydrobromide as defined herein is obtained. Also, the amount of vortioxetine hydrobromide released within the first two hours is kept low which reduces adverse side effects induced by the vortioxetine hydrobromide released in the stomach passage.

In Comparative Example 1, it has been shown that methylcellulose ether-based matrix formulations (which are frequently used) are not suitable for obtaining a dissolution profile as defined herein.

The invention claimed is:

1. A solid oral pharmaceutical composition comprising crystalline vortioxetine hydrobromide in a matrix formed from at least one polyethylene oxide and optionally one or more further matrix forming polymers,
   wherein the at least one polyethylene oxide has a molecular weight Mw of at least 300,000 and not more than about 1,000,000, and the at least one polyethylene oxide is present in the matrix in an amount of 45-95% (w/w) based on the total weight of the matrix.

2. The pharmaceutical composition according to claim 1, wherein vortioxetine hydrobromide is present in the matrix in an amount of 2-25% (w/w) based on the total weight of the matrix.

3. The pharmaceutical composition according to claim 1 wherein the at least one polyethylene oxide is present in the matrix in an amount of 75-98% (w/w) based on the total weight of the matrix.

4. The pharmaceutical composition according to claim 1 wherein the matrix further comprises one or more pharmaceutically acceptable excipients.

5. The pharmaceutical composition according to claim 4, wherein the matrix comprises microcrystalline cellulose in an amount of 0-25% (w/w), based on the total weight of the matrix.

6. The pharmaceutical composition according to claim 1, wherein the vortioxetine hydrobromide is selected from the group consisting of crystalline forms alpha, beta and a crystalline form having an XRPD pattern with characteristic peaks (expressed in 2θ±0.2° 2θ (CuKα radiation)) at 5.5°, 14.8°, 16.7° and 20.0°.

7. The pharmaceutical composition according to claim 1, wherein vortioxetine hydrobromide has a dissolution profile characterized as follows:
   1-20% (w/w) after 30 minutes,
   3-40% (w/w) after 120 minutes,
   at least 75% (w/w) after 600 minutes,
   each based on the total amount of vortioxetine hydrobromide in the pharmaceutical composition of the invention (at the beginning of the measurement (t=0).

8. The pharmaceutical composition according to claim 1, wherein not more than 40% (w/w) of vortioxetine hydrobromide, based on the total weight amount of vortioxetine hydrobromide in the pharmaceutical composition, is released within 2 hours upon administration of the composition to a human patient.

9. The pharmaceutical composition according to claim 1, wherein the pharmaceutical composition is a tablet consisting of the matrix as core and one or more pharmaceutically acceptable coatings.

* * * * *